US008722614B2

(12) United States Patent (10) Patent No.: US 8,722,614 B2
Kato et al. (45) Date of Patent: May 13, 2014

(54) ADIPONECTIN PRODUCTION ENHANCER

(75) Inventors: Norihisa Kato, Higashi-Hiroshima (JP);
Kazunobu Tokunaga, Fujisawa (JP);
Kazuhisa Tsujimoto, Fukui (JP);
Hideyuki Yamada, Fukui (JP)

(73) Assignee: Seiren Kabushiki Kaisha, Fukui-Ken (JP)

( * ) Notice: Subject to any disclaimer, the term of this patent is extended or adjusted under 35 U.S.C. 154(b) by 427 days.

(21) Appl. No.: 12/450,286

(22) PCT Filed: Mar. 21, 2008

(86) PCT No.: PCT/JP2008/055238
§ 371 (c)(1),
(2), (4) Date: Sep. 18, 2009

(87) PCT Pub. No.: WO2008/123128
PCT Pub. Date: Oct. 16, 2008

(65) Prior Publication Data
US 2010/0035810 A1 Feb. 11, 2010

(30) Foreign Application Priority Data
Mar. 23, 2007 (JP) ................................. 2007-077131

(51) Int. Cl.
*A61K 38/00* (2006.01)
*A61K 38/17* (2006.01)
(52) U.S. Cl.
USPC ........................................... 514/1.1; 530/353
(58) Field of Classification Search
None
See application file for complete search history.

(56) References Cited

U.S. PATENT DOCUMENTS

| | | | |
|---|---|---|---|
| 6,165,982 | A | 12/2000 | Yamada et al. |
| 2001/0053759 | A1 | 12/2001 | Jin et al. |
| 2006/0099324 | A1 | 5/2006 | Aurio et al. |
| 2006/0128798 | A1* | 6/2006 | Wang ............................ 514/471 |

FOREIGN PATENT DOCUMENTS

| | | |
|---|---|---|
| EP | 1 201 245 | 5/2002 |
| EP | 1 201 245 A1 | 5/2002 |
| JP | 1-256351 | 10/1989 |
| JP | 10-140154 | 5/1998 |
| JP | 10-265403 | 10/1998 |
| JP | 2000-184868 | 7/2000 |
| JP | 2000-256210 | 9/2000 |
| JP | 2000-312568 | 11/2000 |
| JP | 2001-354584 | 12/2001 |
| JP | 2003-231610 | 8/2003 |
| JP | 2004-18648 | 1/2004 |
| JP | 2004-244371 | 9/2004 |
| JP | 2000-312568 | 11/2004 |
| JP | 2006-232787 | 9/2006 |

OTHER PUBLICATIONS

International Search Report issued Jun. 24, 2008 in International (PCT) Application No. PCT/JP2008/055238.
S. Kakei et al. "Kinu Tanpakushitsu Sericin no Shishitsu Taisha Kaizen Sayo", The 61$^{st}$ Japanese Society of Nutrition and Food Science Taikai Koen Yoshishu, Apr. 20, 2007, p. 193.
S. Zhaorigetu et al., "Silk protein, sericin, suppresses DMBA-TPA-induced mouse skin tumorigenesis by reducing oxidative stress, inflammatory responses and endogenous tumor promoter TNF-α", Oncology Reports, vol. 10, No. 3, pp. 537-543, 2003.
N. Maeda et al., "Adiponectin", Molecular Medicine, vol. 42, No. 1, pp. 11-21, 2005.
N. Maeda et al., "PPARγ Ligands Increase Expression and Plasma Concentrations of Adiponectin, an Adipose-Derived Protein", Diabetes, vol. 50, pp. 2094-2099, Sep. 2001.
K. Nishida et al., "Ko-TNF α Kotai wa Ensho Seigyo Jotai ni Kakawarazu Adiponectin o Zoka Saseru", Folia endocrinologica Japonica, vol. 82, No. 1, p. 124. Apr. 20, 2006.
T. Tadokoro et al., "Shokuhin Miriyo Shigen to Shiteno Silk no Oyo o Mezasu—Silk Tanpakushitsu no Shokuhin Kinosei o Akiraka ni suru Eiyogakuteki Kenkyu", Yasan, vol. 55, pp. 11-14, Jan. 2006.
S. Kurioka et al., "Shoto Fukago no Kettochi ni Oyobosu Sasamayu Nessui Chushutsubutsu no Eikyo", Nippon Silk Gakkaishi, No. 15, pp. 98-99, Dec. 1, 2006.
K. Nozawa et al., "Kinu Tanpakushitsu Sericin no Ketto Teika Sayo", Japan Society for Bioscience, Biotechnology, and Agrochemistry, 2003 Nendo, Taikai Koen Yoshishu, p. 142, Mar. 5, 2003.
H. Minagawa et al., "Suiyosei Sericin no Shokasei Oyobi Ketchu Cholesterol-chi ni Oyobosu Eikyo", The 57$^{th}$ Japanese Society of Nutrition and Food Science Taikai Koen Yoshishu, p. 277, Apr. 1, 2003.
Seikagaku Jiten, (third edition), p. 785, Kabushiki Kaisha Tokyo Kagaku Dojin, Nov. 1998.
S. Kakei et al. "Lipid Metabolism Improving Action of Silk Protein Sericin". The 61$^{st}$ Japanese Society of Nutrition and Food Science Kaikai Koen Yoshishu, Apr. 20, 2007, p. 193.
N. Maeda et al. "Adiponectin". Molecular Medicine, vol. 42, No. 1, pp. 11-21, 2005.
K. Nishida et al. "Anti-TNF-α Antibody Increases Adiponectin Despite State of Controlled Inflammation". Folia endocrinologica Japonica, vol. 82, No. 1, p. 124, Apr. 20, 2006.
T. Tadokoro et al. "Good Information About Wild Silkworm Silk, Aiming at Application of Silk as Unused Resource in Foods". Yasan, vol. 55, pp. 11-14, Jan. 2006.
Kurioka et al. "Effect of Hot Water Extract of Yellow Green Cocoon on Blood Glucose Level After Administration of Sucrose". Nippon Silk Gakkaishi, No. 15, pp. 98-99, Dec. 2006.

(Continued)

*Primary Examiner* — Suzanne M Noakes
(74) *Attorney, Agent, or Firm* — Wenderoth, Lind & Ponack, L.L.P.

(57) ABSTRACT

The present invention relates to an adiponectin production enhancer comprising sericin as an active ingredient, and to a pharmaceutical composition and food and drink comprising sericin. These are effective in the prevention and/or amelioration of various diseases caused by reduction of blood adiponectin level such as arteriosclerosis, fatty liver and diabetes associated with obesity. The enhancer, the pharmaceutical composition and the food and drink according to the invention have excellent adiponectin production enhancing effects as well as high safety and are expected to be broadly applied to a variety of pharmaceutical preparations and food and drink.

7 Claims, No Drawings

(56) References Cited

OTHER PUBLICATIONS

Nozawa et al. "Hypoglycemic Action of Silk Protein Sericin". Japan Society for Bioscience, Biotechnology, and Agrichemistry, 2003, Taikai Koen Yoshishu, p. 142, Mar. 2003.

H. Minagawa et al. "Effect of Water Soluble Sericin on Digestibility and Blood Cholesterol Level". The $57^{th}$ Japanese Society of Nutrition and Food Science Kaikai Koen Yoshishu, p. 277, Apr. 1, 2003.
Extended European Search Report issued Mar. 15, 2011 in European Application No. 08 72 2602.

* cited by examiner

ADIPONECTIN PRODUCTION ENHANCER

This application is a U.S. national stage of International Application No. PCT/JP2008/055238 filed Mar. 21, 2008.

CROSS-REFERENCE TO RELATED APPLICATION

This application is based upon and claims the benefit of priority from the prior Japanese Patent Application No. 2007-077131, filed on 23 Mar. 2007; the entire disclosures of which are incorporated herein by reference.

BACKGROUND OF THE INVENTION

1. Technical Field

The present invention relates to an adiponectin production enhancer comprising sericin as an active ingredient, which can enhance production of adiponectin. The present invention also relates to a pharmaceutical preparation and food and drink which comprise the adiponectin production enhancer, and are effective in prevention and amelioration of various diseases caused by reduction of blood adiponectin levels.

2. Background Art

In modern society, a variety of diseases such as obesity, arteriosclerosis, fatty liver and diabetes have been becoming a huge issue. Conventional treatments of these diseases include pharmacotherapies and many therapeutic agents are known. However, taking of medications may involve side effects such as hypertension, hepatopathy, diarrhea, constipation and headaches, thus, are stressful to patients. In recent years, many approaches for prevention and amelioration of obesity, arteriosclerosis, fatty liver and diabetes have been attempted via dietary habit. Examples of such attempts include intakes of lipolytic agents and dietary fibers, nevertheless, demands for more effective approaches still exist.

Adiponectin is a protein specifically secreted from adipose cells and has been appeared to be closely related to diseases such as obesity, arteriosclerosis, fatty liver and diabetes. Indeed, reduction of blood adiponectin levels in patients suffering from obesity and/or diabetes has been reported (Ouchi, N. et al, Circulation, vol. 100, p. 2473-2476, 1999; and Arita, Y. et al, Biochemical and Biophysical Research Communications, vol. 257, p. 79-83, 1999).

It has also been medically demonstrated that increases of blood adiponectin level ameliorate lifestyle-related diseases such as diabetes (Maeda N. et al., Molecular Medicine, vol. 42, no. 1, p. 11-21, 2005).

Therefore, for the purposes of prevention and/or amelioration of obesity, arteriosclerosis, fatty liver and diabetes, a functional component capable of increasing blood adiponectin level with no or little side effect is desired.

A soybean protein, for example, is known as one of such functional components (Nagasawa et al., Horm. Merab. Res., 34, 635-639, 2002). However, this was not estimated to provide sufficient effect. Extracts from Cordyceps Sinensis Saccardo by hot water (Japanese Patent Application Laid-Open Publication No. 2007-31302) and extracts from Amla (Japanese Patent Application Laid-Open Publication No. 2006-56836) are also known as such functional components. Nevertheless, these components have not been tested for their effect on lipid content in liver, hence, the knowledge concerning these compounds with respect to their efficacy in prevention and amelioration of actual disease state such as fatty liver is not yet sufficient. In addition, these materials and active ingredients are not necessarily easy to obtain.

Sericin is a type of silk proteins and have been reported to have various functions and/or effects such as an antioxidant effect (Japanese Patent Application Laid-Open Publication No. H10 (1998)-140154), preventive effect against colon cancer (Japanese Patent Application Laid-Open Publication No. 2000-256210), weight loss enhancing effect, constipation relieving effect and mineral absorption stimulant effect (Japanese Patent Application Laid-Open Publication No. 2000-312568).

However, to the knowledge of the present inventors, there has been no report that sericin has an adiponectin production enhancing effect.

SUMMARY OF THE INVENTION

The present inventors have now found that sericin, a natural protein found in cocoons and raw silk, has an excellent effect for enhancing of adiponectin production. The present invention is based on this finding.

An object of the present invention is to provide a novel adiponectin production enhancer, which has an excellent effect for enhancing of adiponectin production as well as high safety and can be applied to pharmaceutical preparations and food and drink. Another object of the present invention is to provide a pharmaceutical preparation and food and drink, which are effective in prevention or amelioration of various diseases caused by reduction of blood adiponectin level.

The adiponectin production enhancer according to the present invention comprises sericin as an active ingredient.

In a preferable embodiment of the present invention, the sericin has the average molecular weight of 5,000 to 100,000. In another preferable embodiment, the sericin is hydrolysate of sericin. In still another preferable embodiment, the sericin comprises 20 to 40% by mole of serine in its amino acid composition.

In other words, in the present invention, an active ingredient, sericin, is used for enhancing adiponectin production. In addition, in the present invention, sericin which is an active ingredient is used for the prevention and/or amelioration of a disease or condition caused by reduction of blood adiponectin level.

The pharmaceutical composition according to the present invention comprises the adiponectin production enhancer according to the present invention. The pharmaceutical composition according to the present invention, therefore, can comprise sericin and be used for enhancing adiponectin production in body.

Further, the pharmaceutical composition according to the present invention is used in the prevention and/or amelioration of a disease or condition caused by reduction of blood adiponectin level, and comprises sericin which is the active ingredient of the adiponectin production enhancer. Said disease or condition is, preferably, arteriosclerosis, fatty liver or diabetes associated with obesity or a condition associated therewith.

The food and drink according to the present invention comprises the adiponectin production enhancer according to the present invention.

In another embodiment of the present invention, the food and drink according to the present invention comprises an effective amount of sericin which is the active ingredient of the adiponectin production enhancer and is used for prevention and/or amelioration of a disease or condition caused by reduction of blood adiponectin level. Alternatively, the food and drink according to the invention comprises an effective amount of sericin which is the active ingredient of the adiponectin production enhancer, and has a function to prevent or ameliorate a disease or condition caused by reduction of blood adiponectin level and a functional indication attached thereto.

In a preferable embodiment of the present invention, the food and drink according to the present invention comprises sericin which is an active ingredient in such an amount that provides a range of 10 to 2,000 mg/kg of body weight of sericin to an adult human per day. In still another preferable embodiment, the food and drink is provided in the form of a health food, a functional food, a food for specified health use, a dietary supplement, a food with reduction of a disease risk claim or a medical food.

In another embodiment, the present invention provides a method for enhancing adiponectin production in body, comprising administering an effective amount of sericin which is an active ingredient to a mammal or allowing a mammal to ingest an effective amount of sericin which is an active ingredient. In other words, according to still another embodiment, the present invention provides a method for increasing blood adiponectin level, comprising administering an effective amount of sericin which is an active ingredient to a mammal or allowing a mammal to ingest an effective amount of sericin which is an active ingredient.

In still another embodiment, the invention provides a method for preventing or ameliorating a disease or condition caused by reduction of blood adiponectin level, comprising administering an effective amount of sericin which is an active ingredient to a mammal or allowing a mammal to ingest an effective amount of sericin which is an active ingredient. The disease or condition is, preferably, arteriosclerosis, fatty liver, or diabetes associated with obesity or a condition associated therewith.

In another embodiment, the present invention provides use of sericin which is an active ingredient for the manufacture of an adiponectin production enhancer.

In still another embodiment, the invention provides use of sericin which is an active ingredient in the manufacture of a pharmaceutical composition or food and drink used for preventing or ameliorating a disease or condition caused by reduction of blood adiponectin level. The disease or condition is, preferably, arteriosclerosis, fatty liver, or diabetes associated with obesity or a condition associated therewith.

The adiponectin production enhancer according to the invention has an excellent adiponectin production enhancing effect, while having no or little risk of causing side effect since it uses materials derived from natural substances which have been approved as safe. Therefore, the adiponectin production enhancer can be appropriately incorporated into daily diet and ingested with ease. The present invention also provides a pharmaceutical preparation (i.e., a pharmaceutical composition) and food and drink (i.e., a food composition), comprising an adiponectin production enhancer. The adiponectin production enhancer, pharmaceutical preparation and food and drink according to the invention are highly safe and capable of prominently increasing blood adiponectin level. Therefore, they are highly useful in prevention and amelioration of various diseases such as arteriosclerosis, fatty liver and diabetes associated with obesity.

DETAILED DESCRIPTION OF THE INVENTION

Active Ingredient

In the invention, sericin is used as an active ingredient and can be obtained by extracting sericin as a natural protein found in cocoons and raw silk. More specifically, for example, materials such as cocoons and raw silk can be treated by boiling in hot water thereby being dissolved in water. In treatment, an acid(s), alkali(es) or enzyme(s) may be applied to hydrolyze sericin if necessary. Thus, the term "sericin" as used herein includes not only unhydrolyzed sericin but also hydrolyzed one. Then, the extract is subjected to separation and purification to produce a highly purified aqueous sericin solution. Further, sericin can be obtained as a solid by further subjecting said aqueous solution to a treatment such as hot air drying, vacuum drying and freeze drying.

The molecular weight of the thus obtained sericin is generally distributed within a range of 500 to 500,000, and sericin having any molecular weight within the range can be used for the invention. In a preferably embodiment of the present invention, an average molecular weight of sericin is 5,000 to 100,000, more preferably 10,000 to 50,000, and still more preferably 20,000 to 40,000. In case where sericin has an average molecular weight less than 5000, the adiponectin production enhancing effect may decrease. On the other hand, when sericin has an average molecular weight exceeding 100,000, the water solubility of sericin reduces, and in turn, the ease of handling is decreased, and the effect to be exerted by sericin may also decrease due to the reduction of water solubility.

Natural and unhydrolyzed sericins are known to include multiple components having different molecular weights. For example, in Japanese Patent Application Laid-Open Publication No. 2002-128691, sericins having molecular weights of 400,000, 250,000, 200,000 and 35,000 are identified, respectively. The extract with sericins which are natural proteins contains such sericins being mixed. Further, sericin molecules may bind one another by hydrogen bonds, thereby increasing apparent molecular weight thereof. Accordingly, the extract in which sericin is hydrolyzed by reacting with an acid(s), alkali(es) or enzyme(s) is a mixture containing a further variety of molecular species. In the invention, if needed, sericin (preferably, hydrolyzed sericin) having an average molecular weight in a range of 5,000 to 100,000 can be selectively prepared by controlling conditions such as the agents, concentrations, temperatures and durations. Specifically, such hydrolyzed sericins can be obtained by following methods in Examples as described below.

In a preferable embodiment of the present invention, sericin contains 20 to 40% by mole of serine in its amino acid composition. In case where serine content is less than 20% by mole, the adiponectin production enhancing effect may decrease.

The sericin (hydrolyzed sericin, preferably) used for the invention is easy to dissolve in water, and able to maintain stable properties in the form of an aqueous solution, thereby displaying an excellent miscibility with ingredients generally added to pharmaceutical preparations and food and drink. In addition, sericin is non-toxic, tasteless, and odorless and, meanwhile, highly safe. Therefore, sericin is free of concerns with respect to influences on organoleptic property such as smell and taste and occurrence of side effect, hence, can be appropriately incorporated into daily diet and ingested with ease. Sericin retains its property of the state being a natural protein, hence, is harmless even when ingested in a large amount, and can be utilized as a nutrient source in body.

Sericin, the active ingredient according to the present invention, has an effect that enhances adiponectin production and significantly increases blood adiponectin level. Specifically, the active ingredient according to the present invention was actually demonstrated to remarkably increase blood adiponectin levels, and decrease serum levels of triglycerides, cholesterols and phospholipids (see Evaluation B in Evaluation Test in Examples as described below). In addition, reduction of triglyceride level in liver was also confirmed, hence, the usefulness of the present invention for prevention of fatty liver was proven (see Evaluation C in the Evaluation Test). Furthermore, ingestion of the active ingredient according to the present invention did not affect changes in body weight and adipose tissue quantity, so that no risk of side effect was practically confirmed (see Evaluation A in the Evaluation Test).

Since the active ingredient according to the present invention can significantly increase blood adiponectin level, it is clearly useful in preventing and/or ameliorating a disease or condition caused by reduction of blood adiponectin level. The wording "prevention and/or amelioration of a disease or condition" as used herein includes prevention and/or regulation of the onset or development of the disease, or condition or a symptom associated therewith, and control, delaying or alleviation of the progress of the disease, and prevention or suppression of the recurrence of the disease.

Typical examples of the disease or condition caused by reduction of blood adiponectin level include a lifestyle-related disease, metabolic syndrome (metabolic disorder syndrome) and/or a disease or condition associated therewith, and preferably, arteriosclerosis, fatty liver, or diabetes associated with obesity or a condition associated therewith.

In another embodiment, the present invention provides a method for enhancing adiponectin production in body, comprising administering to or allowing a mammal to ingest an effective amount of sericin. In still another embodiment, the invention provides a method for preventing or ameliorating a disease or condition caused by reduction of blood adiponectin level, comprising administering to or allowing a mammal to ingest an effective amount of sericin. The term "effective amount" as used herein refers to the least amount of the active ingredient that is required to enhance adiponectin production and to exert desired effects such as preventive and/or ameliorative effects.

Adiponectin Production Enhancer

The adiponectin production enhancer according to the present invention comprises sericin as an active ingredient.

The phrase "comprise as an active ingredient" means that the enhancer according to the present invention contains sericin in an amount sufficient to exert its desired adiponectin production enhancing effect (i.e., an effective amount).

Accordingly, sericin can be used as an adiponectin production enhancer as it is, however, the enhancer according to the present invention may further contain a physiologically acceptable carrier and/or additional additive depending on the desired form of the product as long as the enhancer contains the active ingredient in the amount described above and does not adversely affect the adiponectin production enhancing effect. Examples of such a carrier and additive include excipients, binding agents, flavors, buffers, thickening agents, coloring agents, stabilizing agents, emulsifiers, dispersant agents, suspending agent, disintegrators, lubricants and preservatives. The enhancer according to the present invention may be administered or ingested either orally or parenterally. Examples of a form for oral administration include solid formulations such as foods, food additives, tablets, powders, subtle granules, granules, capsules, pills and controlled release agents, and liquid formulations such as solutions, suspensions and emulsions. Examples of a form for parenteral administration include injections, instillations, external preparations and suppositories. These can be formulated or made into a final product by a conventional method routinely used in the art, optionally, in combination with a carrier(s) and/or additive(s).

In order to exert a desired adiponectin production enhancing effect, the active ingredient according to the present invention is desirably administered or ingested in such an amount that provides a range of 10 to 2000 mg/kg of body weight of sericin to an adult human per day, and a preferable amount to be administered or ingested is 10 to 500 mg/kg, and more preferably, 20 to 200 mg/kg. In case where the amount to be administered or ingested per day is less than 10 mg, a sufficient effect may not be exerted. On the other hand, the effect is not expected to be further enhanced by administrating or ingesting more than 2000 mg. According to the present invention, the active ingredient in this amount may be administered or ingested as an enhancer as it is or in other desired forms such as a pharmaceutical preparation or food and drink at once or in several times a day.

The adiponectin production enhancer according to the present invention can be used either alone or incorporated as an additive into various composition such as pharmaceutical compositions and food and drink to produce a composition having an adiponectin production enhancing effect.

Pharmaceutical Preparation

As described above, the pharmaceutical composition according to the present invention comprises the adiponectin production enhancer according to the present invention. The pharmaceutical composition desirably comprises the adiponectin production enhancer in an appropriate amount so as to contain an effective amount of the active ingredient of the enhancer.

In another embodiment, as described above, the pharmaceutical composition according to the present invention is used for preventing and ameliorating a disease or condition caused by reduction of blood adiponectin level, and comprises sericin which is the active ingredient of the adiponectin production enhancer. In this case, also, the pharmaceutical composition desirably contains an effective amount of sericin which is the active ingredient of the adiponectin production enhancer, alternatively, the pharmaceutical composition may contain an appropriate amount of the adiponectin production enhancer so as to contain effective amount of the active ingredient.

Therefore, the pharmaceutical composition according to the present invention comprises sericin in a sufficient amount to exert an desirable effect (i.e., an effective amount), and is one prepared for either oral or parenteral administration in combination with a pharmaceutically acceptable additive(s) according to a conventional method. Examples of such a pharmaceutically acceptable additive include excipients, stabilizing agents, preservatives, wetting agents, emulsifiers, lubricants, sweeteners, coloring agents, flavors, buffers, antioxidants, pH control agents, binding agents, thickening agents, dispersants, suspending agents and disintegrators. In case where the pharmaceutical composition according to the present invention is a formulation for oral administration, it may take forms of solid formulations such as tablets, powders, subtle granules, granules, capsules, pills and controlled release agents, and liquid formulations such as solutions, suspensions and emulsions. In case where the pharmaceutical composition is a formulation for parenteral administration, it may take forms of injections, instillations, external preparations and suppositories. The pharmaceutical composition is preferably a formulation for oral administration in view of convenience.

The pharmaceutical composition according to the present invention may further comprise adjuvants if needed.

Examples of other adjuvants that can be used in combination with the active ingredient include vitamin ingredients (e.g., vitamin C and vitamin E), antibiotics, amino acids, peptides, minerals (e.g., zinc, iron, copper and manganese), nucleic acids, polysaccharides, fatty acids and crude drugs.

In formulation, one or more of medically effective components (active ingredients) other than the active ingredient according to the present invention may be further added to and combined therewith. In administration of the active ingredient according to the present invention, it may be administered in combination with one or more of medically effective components other than the active ingredient according to the present invention. Examples of such other effective components (active ingredients) include insulin, sulfonylurea based agents, thiazoline based agents and alpha-glucosidase inhibitors.

Food and Drink

As described above, the food and drink according to the present invention comprises the adiponectin production enhancer according to the present invention. The food and drink desirably comprises the adiponectin production enhancer in an appropriate amount so as to contain an effective amount of the active ingredient of the enhancer.

In another embodiment, as described above, the food and drink according to the present invention comprises sericin which is the active ingredient of the adiponectin production enhancer in an effective amount, and used for preventing and ameliorating a disease or condition caused by reduction of blood adiponectin level.

The phrase "comprise an active ingredient in an effective amount" means to contain the active ingredient in an amount so as to exert the effect of the active ingredient as a result of ingesting the food and drink in an amount generally taken as a meal.

The active ingredient according to the present invention may be added to the food and drink as it is or in the form of an enhancer as described above. The food and drink according to the present invention may be one prepared adding a conventionally used additive(s) such as a stabilizer; one prepared further adding thereto various proteins, sugars, fats, trace elements, vitamins and the like; one in the form of liquid, semi-liquid, solid or paste; or one to which an effective component(s) usually added to food and drink is/are added.

In the present invention, "a food and drink" means what mammals can in-take, and is other than pharmaceutical preparations, without any other particular restrictions. It may be in any of a liquid (a solution, suspension and emulsion), semi-liquid, powder or solid form. Therefore, the food and drink may be, for example, in the form of a beverage or tablet of a dietary supplement.

Specific examples of the food and drink include instant foods such as instant noodles, retort foods, canning, microwave cooked food, instant soups/miso soups and freeze dried food; beverages such as soft drinks, fruit drinks, vegetable drinks, soy milks, coffees, teas, powder drinks, concentrated drinks, nutritional beverages and alcohol drinks; wheat product such as bread, pasta, noodles, cake mix, frying flour and bread crumb; confectioneries such as candies, caramels, chewing gums, chocolates, cookies, biscuits, cakes, pies, crispy snacks, crackers, Japanese confectioneries and dessert confectioneries; seasonings such as sauce, tomato-processed seasonings, flavors, seasoning mix, soy-based sauce, dressings, dippings and roux for curry and stew; fats and oils such as processed fats and oils, butters, margarines and mayonnaises; dairy products such as milk-based drinks, yoghurts, lactic acid bacteria beverages, ice creams and creams; processed marine products such as fish hams and sausages and fish-paste products; processed livestock products such as meat hams and sausages; processed agricultural products such as cannings of agricultural products, jams and marmalades, pickled or salted vegetables, cooked beans and cereals; frozen foods; and nutritional foods.

The food and drink according to the present invention may be preferably applied to a person who has a decreased blood adiponectin level, one suspected to have a decreased blood adiponectin level, or one being at a high risk of having a decreased blood adiponectin level. The food and drink according to the present invention may be preferably applied to a person affected with a disease caused by reduction of blood adiponectin level or one being at a high risk of being affected with such a disease.

A person being at a high risk of having a decreased blood adiponectin level, or one being at a high risk of being affected with a disease caused by reduction of blood adiponectin level includes a person who has been judged as being at such a risk based on his/her daily life style such as dietary style or based on a result of diagnosis/consultation such as a medical examination or one who has been identified as being at such a risk by himself/herself own or by his/her surroundings.

The term "food and drink" as used herein includes a product which is categorized as a health food, a functional food, a food for specified health use, a dietary supplement, a food with reduction of a disease risk claim or a medical food. Further, the term "food and drink" may be used to include fodders when applied to mammals other than human. As used herein, the term "food for specified health use" refers to a food wherein production or distribution thereof on purposes of prevention or amelioration of a disease or condition caused by reduction of blood adiponectin level, may be restricted to some extent by laws in some countries (such as Japan) with respect to health consideration. Such a food product may be one having an indication showing that the product may reduce risks of certain diseases, i.e., a food product with reduction of disease risk claim. The term "reduction of a disease risk claim" used herein refer to an indication of a food product which may reduce a risk of a disease, and may be any of the indications defined or approved based on a standard defined by Joint FAO/WHO Food Standards Programme (Codex Alimentarius Commission) or in reference to the standard.

A component having a different function may be added to the food and drink according to the present invention in addition to the active ingredient described above. For example, combination of the active ingredient according to the present invention with a food product which is ingested on everyday life, health food, functional food and supplement (e.g., a food product containing one or more of minerals such as calcium and magnesium and vitamins such as vitamin K) may provide a food and drink having a function based on the additional ingredient in addition to the effect exerted by the invention.

In another embodiment, the present invention provide a food and drink which comprises an effective amount of sericin which is the active ingredient of the adiponectin production enhancer, wherein the food and drink has a function of preventing or ameliorating a disease or condition caused by reduction of blood adiponectin level and an indication of said function attached thereto. The indication to be attached to the food and drink may be attached to, for example, any of the body, vessel, package, instruction, package insert or advertisement of the product.

In production of the food and drink according to the present invention, a sugar(s), flavor(s), fruit juice(s), food additive(s) and stabilizing agent(s), which is used in general formulation of food and drink, may be appropriately added thereto. Production of the food and drink may be carried out by referring to a known manufacturing technique in the art. The food and drink according to the present invention may take a variety of forms, and be produced according to a known manufacturing technique for pharmaceutical preparations. In this case, the food and drink may be produced by using a carrier(s) and additive(s) described in the items referring to the production of the enhancer and pharmaceutical composition according to the invention. Alternatively, the food and drink may be produced as a multi-functional food and drink by combining with a component(s) having a function(s) different from that of the invention or with a different functional food product(s).

In administration or ingestion of the pharmaceutical composition and food and drink according to the present invention, the amount of the active ingredient according to the present invention to be administered or ingested may be determined based on the recipient, age and body weight of the recipient, symptoms, duration of administration, dosage form, manner of administration, combination of the agents and the like. In the invention, it is desirable to appropriately determine the content of the active ingredient in the composition or food and drink considering the dose or intake of the composition or food and drink per day, so that the active ingredient in the amount that is at least required for enhancement of adiponectin production per day can be administered or ingested.

Accordingly, the pharmaceutical composition or the food and drink according to the present invention preferably comprises sericin which is an active ingredient in such an amount that provides a range of 10 to 2,000 mg/kg of body weight of sericin to an adult human per day.

The amount of the active ingredient to be contained in the pharmaceutical composition or food and drink according to the present invention may be defined as the content of the active ingredient therein. In this case, based on an assumption that an adult human has the body weight of 60 kg, the amount of the active ingredient to be administered to or ingested by an adult human having the body weight of 60 kg per day is calculated. Subsequently, the content of the active ingredient in the pharmaceutical composition or food and drink can be calculated based on the amount of the pharmaceutical composition or food and drink that can be actually administered or ingested.

Accordingly, for an exemplary content of the active ingredient in the pharmaceutical composition or food and drink, the pharmaceutical composition according to the present invention contains the active ingredient in an amount of 0.1 to 70% by weight, preferably, 0.5 to 50% by weight relative to the entire amount of the composition. On the other hand, the food and drink according to the present invention contains the active ingredient, for example, in an amount of 0.1 to 70% by weight, preferably, 0.5 to 50% by weight relative to the entire amount of the food and drink.

EXAMPLES

The present invention is further illustrated by the following Examples that are not intended as a limitation of the invention. The data obtained in the study below were subjected to significant tests in accordance with Student's t-Test. In this study, "%" indicates "% based on weight" unless otherwise stated.

Preparation of Hydrolyzed Sericin:

Hydrolyzed sericin, the active ingredient of the adiponectin production enhancer according to the present invention, was prepared. In brief, a silk fabric comprising raw silk was treated with 0.2% of sodium carbonate (pH 11 to 12) at 95° C. for 2 hours, and hydrolyzed sericin was extracted therefrom. The obtained extract was filtered through a filter having an average pore size of 0.2 μm to remove aggregates, after which the filtrate was desalted using a reverse osmosis membrane to obtain a colorless purified solution having a concentration of 0.2%. The purified solution was concentrated up to a concentration of about 2% using an evaporator, and then subjected to freeze drying to obtain the powder form of the hydrolyzed sericin. The distribution of the molecular weight of the hydrolyzed sericin was in the range of 5,000 to 7,000 with the average molecular weight of 30,000. The hydrolyzed sericin contained 35% by mole of serine in its amino acid composition.

Evaluation Test:

Male Sprague Dawley (SD) rats in the age of 4 weeks were used as animal models. The rats were assigned to a control group (12 rats) and adiponectin production enhancer group (12 rats) so as to allow both groups to have almost equivalent average body weights. The rats were fed with the indicated experimental foods (see Table 1) in constant consumable amounts daily for 35 days.

In detail, the adiponectin production enhancer group was ingested with a diet (containing 20% casein) in which 4% of hydrolyzed sericin had been added to a meal containing 20% of beef tallow, whereas the control group was ingested with a diet containing 24% casein without addition of hydrolyzed sericin.

TABLE 1

|  | Control Group (% by weight) | Adiponectin Production Enhancer Group (% by weight) |
| --- | --- | --- |
| Casein[1] | 24 | 20 |
| Hydrolyzed sericin[2] | 0 | 4 |
| L-cystine | 0.2 | 0.2 |
| Beef tallow | 20 | 20 |
| Cellulose | 5 | 5 |
| Vitamin mix[3] | 1 | 1 |
| Salt mix[4] | 3.5 | 3.5 |
| Sucrose | 20 | 20 |
| Corn starch | 26.3 | 26.3 |

Notes:
[1]Casein (N × 6.25), 87.0%
[2]Hydrolyzed sericin (N × 6.25), 92.9%
[3]AIN-93
[4]AIN-93G
(AIN-93 and AIN-93G are well known standard fodder compositions defined by American Institute of Nutrition (AIN)).

Evaluation A: Effect of Hydrolyzed Sericin on Body Weight and Organ Weight

Rats were bred for 35 days in accordance with Evaluation Test above, and then sacrificed under ether anesthesia to extract livers and adipose tissues. At the same time, serum was collected from the blood and subjected to analyses as described below.

Table 2 shows the body weights and weights of the organs of the rats after breeding.

During the breeding period of 35 days, difference in increase of the body weight and the adipose tissue weight were not observed between these groups, indicating that ingestion of sericin does not adversely affect growth.

TABLE 2

|  | Control Group | Adiponectin Production Enhancer Group |
| --- | --- | --- |
| Initial Body Weight (g) | 99 ± 2 | 99 ± 2 |
| Final Body Weight (g) | 336 ± 4 | 327 ± 3 |
| Amount Ingested (g/35 days) | 589 ± 0 | 589 ± 0 |
| Liver Weight (g) | 13.8 ± 0.3 | 13.1 ± 0.2 |
| Liver Weight (%) | 4.11 ± 0.09 | 3.99 ± 0.05 |

TABLE 2-continued

|  | Control Group | Adiponectin Production Enhancer Group |
|---|---|---|
| Adipose Tissue Weight (g) | 14.2 ± 0.7 | 12.8 ± 0.9 |
| Adipose Tissue Weight (%) | 4.22 ± 0.18 | 3.92 ± 0.27 |

Note:
Each value in the table is expressed with the average ± SE (n = 12).

Evaluation B: Effect of Hydrolyzed Sericin on Various Parameters in Serum

The lipid level in the serum collected as described above was measured by an enzymatic method using a commercially available kit.

Specifically, the levels of triglyceride, cholesterol and phospholipid were measured using Triglyceride E-Test Wako, Cholesterol E-Test Wako and Phospholipid C-Test Wako (all from Wako Pure Chemical Industries, Ltd., Japan), respectively. The lipid peroxide level was measured in terms of the quantity of thiobarbituric acid reactive substances (TBARS) by a conventional method in accordance with Yagi method (K. Yagi, Biochem. Med., 15, 212.216, 1976).

Each level of adiponectin, resistin and leptin was measured by enzyme immunoassay using a commercially available kit.

Specifically, the levels of adiponectin, resistin and leptin were measured using Mouse/Rat Adiponectin ELISA Kit (Otsuka Pharmaceutical Co., Ltd., Japan), Rat Resistin ELISA Kit (B-Bridge International, Inc., USA) and Mouse/Rat Leptin ELISA Kit (B-Bridge International, Inc., USA), respectively.

The results are shown in Table 3.

Serum levels of triglyceride, cholesterol and phospholipid, which are considered as indicators of various diseases associated with obesity, were clearly reduced in the adiponectin production enhancer group.

Serum levels of resistin and leptin did not considerably differ between the control and adiponectin production enhancer groups, however, the adiponectin level was significantly increased in the adiponectin production enhancer group.

This result reveals that the adiponectin production enhancer according to the present invention contributes to prevention or amelioration of diseases associated with obesity such as arteriosclerosis by elevating serum adiponectin level.

TABLE 3

|  | Control Group | Adiponectin Production Enhancer Group |
|---|---|---|
| Triglyceride (mg/100 ml) | 384 ± 42 | 259 ± 28* |
| VLDL-Triglyceride (mg/100 ml) | 271 ± 30 | 173 ± 6* |
| LDL-Triglyceride (mg/100 ml) | 31 ± 2 | 30 ± 4 |
| HDL-Triglyceride (mg/100 ml) | 9.3 ± 0.7 | 6.1 ± 0.3 |
| Cholesterol (mg/100 ml) | 97 ± 4 | 81 ± 3* |
| VLDL-Cholesterol (mg/100 ml) | 16 ± 1 | 13 ± 1* |
| LDL-Cholesterol (mg/100 ml) | 17 ± 1 | 13 ± 1* |
| HDL-Cholesterol (mg/100 ml) | 40 ± 3 | 35 ± 2 |
| Phospholipid (mg/100 ml) | 232 ± 11 | 191 ± 7* |
| VLDL-Phospholipid (mg/100 ml) | 34 ± 4 | 26 ± 2 |
| LDL-Phospholipid (mg/100 ml) | 24 ± 1 | 19 ± 1* |
| HDL-Phospholipid (mg/100 ml) | 81 ± 4 | 69 ± 3 |

TABLE 3-continued

|  | Control Group | Adiponectin Production Enhancer Group |
|---|---|---|
| Lipid Peroxide (μmol/100 ml) | 3.90 ± 0.37 | 3.95 ± 0.42 |
| Adiponectin (ng/100 ml) | 284 ± 44 | 465 ± 24* |
| Leptin (ng/100 ml) | 38.7 ± 5.5 | 35.7 ± 7.2 |
| Resistin (μg/100 ml) | 2.72 ± 0.20 | 2.59 ± 0.14 |

Note:
Each value in the table is expressed with the average ± SE (n = 7 to 10).
*P < 0.05

Evaluation C: Effect of Hydrolyzed Sericin on Lipid Level in Liver

Hepatic lipid was extracted by a conventional method in accordance with a method by Folch et al (Folch J., Lees M., Sloane-Stanley G. H. A simple method for the isolation and purification of total lipids from animal tissues. J Biol. Chem., 226, 497-509, 1957).

After the extraction of hepatic lipid, the lipid level was measured according to the method described in Evaluation B above.

The results are shown in Table 4.

In the adiponectin production enhancer group, the triglyceride level was clearly reduced. Accumulation of triglyceride in the liver is considered as an indicator of certain diseases such as fatty liver. Therefore, the decrease of triglyceride in the liver due to the ingestion of the adiponectin production enhancer according to the present invention was found to be highly beneficial for prevention of fatty liver.

TABLE 4

|  | Control Group | Adiponectin Production Enhancer Group |
|---|---|---|
| Triglyceride (mg/g tissue) | 23.5 ± 2.0 | 15.7 ± 1.3* |
| Cholesterol (mg/g tissue) | 1.74 ± 0.19 | 1.82 ± 0.23 |
| Phospholipid (mg/g tissue) | 22.5 ± 0.5 | 22.7 ± 0.4 |
| Lipid Peroxide (nmol/g tissue) | 155 ± 2 | 162 ± 6 |

Note:
Each value in the table is expressed with the average ± SE (n = 12).
*P < 0.05

The invention claimed is:

1. A method for enhancing adiponectin production in the body of a mammal in need thereof, comprising:
    administering a therapeutically effective amount of an adiponectin production enhancer composition consisting of 0.5 to 50% by weight of sericin hydrolysate relative to the entire composition as an active ingredient to the mammal, or
    allowing the mammal to ingest a therapeutically effective amount of the adiponectin production enhancer composition.

2. A method for treating or ameliorating a disease or condition caused by a reduction of a blood adiponectin level in a mammal in need thereof, comprising:
    administering a therapeutically effective amount of an adiponectin production enhancer composition consisting of 0.5 to 50% by weight of sericin hydrolysate relative to the entire composition as an active ingredient to the mammal, or
    allowing the mammal to ingest a therapeutically effective amount of the adiponectin production enhancer composition.

3. The method according to claim 1, wherein said disease or condition is arteriosclerosis, fatty liver, or diabetes associated with obesity, or a condition associated with said disease or condition.

4. The method according to claim 1, wherein said sericin hydrolysate has an average molecular weight of 5,000 to 100,000.

5. The method according to claim 1, wherein said sericin hydrolysate comprises 20 to 40% by mole of serine in its amino acid composition.

6. The method according to claim 2, wherein said sericin hydrolysate has an average molecular weight of 5,000 to 100,000.

7. The method according to claim 2, wherein said sericin hydrolysate comprises 20 to 40% by mole of serine in its amino acid composition.

\* \* \* \* \*